United States Patent
Zhou et al.

(10) Patent No.: US 8,926,972 B2
(45) Date of Patent: Jan. 6, 2015

(54) ANTI-ANGIOGENESIS FUSION PROTEINS

(75) Inventors: Joe Zhou, Shanghai (CN); Jianyang Zhao, Shanghai (CN); Jiuru Sun, Box Hill North (AU); Jun Wang, Shanghai (CN); Shaoxiong Wang, Shanghai (CN); Xinxing Ma, Shanghai (CN); Jun Lin, Shanghai (CN)

(73) Assignee: Genor Biopharma Co. Ltd, Shanghai (CN)

( * ) Notice: Subject to any disclaimer, the term of this patent is extended or adjusted under 35 U.S.C. 154(b) by 341 days.

(21) Appl. No.: 12/727,188

(22) Filed: Mar. 18, 2010

(65) Prior Publication Data

US 2010/0331250 A1    Dec. 30, 2010

Related U.S. Application Data

(60) Provisional application No. 61/163,203, filed on Mar. 25, 2009.

(30) Foreign Application Priority Data

Mar. 18, 2009  (CN) .......................... 2009 1 0056955
Mar. 18, 2010  (WO) ................. PCT/CN2010/071125

(51) Int. Cl.
*A61K 38/18*      (2006.01)
*C07K 14/71*      (2006.01)
*A61K 38/00*      (2006.01)

(52) U.S. Cl.
CPC ............. *C07K 14/71* (2013.01); *C07K 2319/30* (2013.01); *A61K 38/00* (2013.01)
USPC ..... 424/134.1; 424/192.1; 514/1.1; 514/13.3; 514/21.2; 530/350

(58) Field of Classification Search
None
See application file for complete search history.

(56) References Cited

U.S. PATENT DOCUMENTS

| | | | |
|---|---|---|---|
| 5,952,199 A | 9/1999 | Davis-Smyth et al. | |
| 6,100,071 A | 8/2000 | Davis-Smyth et al. | |
| 6,383,486 B1 | 5/2002 | Davis-Smyth et al. | |
| 6,461,864 B1 | 10/2002 | Soriano et al. | |
| 6,897,294 B2 | 5/2005 | Davis-Smyth et al. | |
| 7,070,959 B1 * | 7/2006 | Papadopoulos et al. | 435/69.7 |
| 7,750,138 B2 | 7/2010 | Fang et al. | |
| 7,771,721 B2 | 8/2010 | Davis-Smyth et al. | |

FOREIGN PATENT DOCUMENTS

| | | |
|---|---|---|
| JP | 2000-502357 | 2/2000 |
| JP | 2003-501089 | 1/2003 |
| JP | 2008-503243 | 2/2008 |
| WO | WO-97/44453 | 11/1997 |
| WO | WO-00/75319 | 12/2000 |
| WO | WO-2006/076288 | 7/2006 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Akerstrom et al., J. Biol. Chem. (1986) 261:10240-10247.
Bjorck et al., J. Immunol. (1984) 133:969-974.
Christinger et al., J. Biol. Chem. (2004) 279(11):10382-10388.
Deer et al., Biotechnol. Prog. (2004) 20:880-889.
Durocher et al., Nucleic Acids Research (2002) 30:E9.
Eliasson et al., J. Biol. Chem. (1988) 263:4323-4327.
Ferrara, Endocrine Rev. (2004) 25(4):581-611.
Ferrara et al., Nature Medicine (2003) 9(6):669-676.
Ferrara et al., Nature Rev. Drug Disc. (2004) 3:391-400.
Fischer et al., Cell (2007) 131:463-475.
Folkman et al., Science (1987) 235:442.
Gentz et al., PNAS USA (1989) 86:821-824.
Guss et al., EMBO J. (1986) 5:1567-1575.
Hanahan and Folkman, Cell (1996) 86:353-364.
Hjelm et al., Eur. J. Biochem. (1975) 57:395-403.
Kozak, Journal of Biological Chemistry (1991) 266:19867-19870.
Kuo et al., PNAS USA (2001) 98:4605-4610.
Morton and Myszka, Methods in Enzymology (1998) 295:268.
Sikkema, Amer. Biotech. Lab. (1989) 7:42.
Sjoquist et al., Eur. J. Biochem. (1972) 29:572-578.
Welford, Opt. Quant. Elect. (1991) 23:1.
Wilson et al., Cell (1984) 37:767-778.
Zambrowiez et al., PNAS USA (1997) 94:3789-3794.
Davis-Smyth et al., "The second immunoglobulin-like domain of the VEGF tyrosine kinase receptor Flt-1 determines ligand binding and may initiate a signal transduction cascade," EMBO J (1996) 15(18):4919-4927.
Final Office Action in JP-2012-500054, (English language translation dated Mar. 13, 2014,) 3 pages.

* cited by examiner

*Primary Examiner* — Christine J Saoud
*Assistant Examiner* — Jon M Lockard
(74) *Attorney, Agent, or Firm* — Morrison & Foerster LLP

(57) ABSTRACT

The disclosure provides a novel anti-angiogenesis fusion protein. The present invention combines a chimeric vascular endothelial cell growth factor (VEGF) receptor or a fragment thereof with a multimerizing component, which have a superior binding capacity with human VEGF and placental growth factor (PIGF). The fusion protein has improved stability, prolonged half-life and the ability to form multivalent interactions with VEGF, and can be used for anti-angiogenesis, treating VEGF related diseases and inhibiting tumor growth.

18 Claims, 8 Drawing Sheets

Flt1 Sp
MVSYWDTGVL LCALLSCLLL TGSSSGSKLK DPELSLKGTQ HIMQAGQTLH LQCRGEAAHK WSLPEMVSKE SERLSITKSA
                                                                    Flt1D1
CGRNGKQFCS TLTLNTAQAN HTGFYSCKYL AVPTSKKKET ESAIYIFISD TGRPFVEMYS
        Flt1D2
EIPEIIHMTE GRELVIPCRV TSPNITVTLK KFPLDTLIPD GKRIIWDSRK GFIISNATYK EIGLLTCEAT
                                                    Flt1D3
VNGHLYKTNY LTHRQTNTII DVQISTPRPV KLLRGHTLVL NCTATTPLNT RVQMTWSYPD EKNKRASVRR RIDQSNSHAN
IFYSVLTIDK MQNKDKGLYT CRVRSGPSFK SVNTSVHIYD KAFITVKHRK QQVLETVAGK
Flt2D4
RSYRLSMKVK AFPSPEVVWL KDGLPATEKS ARYLTRGYSL IIKDVTEEDA GNYTLLSIK QSNVFKNLTA
                        Flt1D5
TLIVNVKPQI YEKAVSSFPD PALYPLGSRQ ILTCTAYGIP QPTIKWFWHP CNHNHSEARC DFCSNNEESF ILDADSNMGN
RIESITQRMA IIEGKNKMAS TLVVADSRIS GIYICIASNK VGTVGRNISF YITDVPNGFH
                Flt1D6
VNLEKMPTEG EDLKLSCTVN KFLYRDVTWI LLRTVNNRTM HYSISKQKMA ITKEHSITLN LTIMNVSLQD
                                                            Flt1D7
SGTYACRARN VYTGEEILQK KEITIRDQEA PYLLRNLSDH TVAISSSTTL DCHANGVPEP QITWFKNNHK IQQEPGIILG
PGSSTLFIER VTEEDEGVYH CKATNQKGSV ESSAYLTVQG TSDKSNLELI TLT

FIG. 1A

KDR sp
MQSKVLLAVA LMLCVETRAA SVGLPSVSLD LPRLSIQKDI LTIKANTTLQ ITCRGQRDLD WLWPNNQSGS EQRVEVTECS
KDR D1
DGLFCKTLTI PKVIGNDTGA YKCFYRETDL ASVIYVYVQD YRSPFIASVS DQHGVVYITE
KDR D2
NKNKTVVIPC LGSISNLNVS LCARYPEKRF VPDGNRISWD SKKGFTIPSY MISYAGMVFC EAKINDESYQ
SIMYIVVVVG YRIYDVVLSP SHGIELSVGE KLVLNCTART ELNVGIDFNW EYPSSKHQHK KLVNRDLKTQ SGSEMKKFLS
KDR D3
TLTIDGVTRS DQGLYTCAAS SGLMTKKNST FVRVHEKPFV AFGSGMESLV EATVGERVRI
KDR D4
PAKYLGYPPP EIKWYKNGIP LESNHTIKAG HVLTIMEVSE RDTGNYTVIL TNPISKEKQS HVVSLVVYVP
KDR D5
PQIGEKSLIS PVDSYQYGTT QTLTCTVYAI PPPHHIHWYW QLEEECANEP SQAVSVTNPY PCEEWRSVED FQGGNKIEVN
KNQFALIEGK NKTVSTLVIQ AANVSALYKC EAVNKVGRGE RVLSFHVTRG PEITLQPDMQ
KDR D6
PTEQESVSLW CTADRSTFEN LTWYKLGPQP LPIHVGELPT PVCKNLDTLW KLNATMFSNS TNDILIMELK
KDR D7
NASLQDQGDY VCLAQDRKTK KRHCVVRQLT VLERVAPTIT GNLENQTTSI GESIEVSCTA SGNPPPQIMW FKDNETLVED
SGIVLKDGNR NLTIRRVRKE DEGLYTCQAC SVLGCAKVEA FFIIEGAQEK TN

*FIG. 1B*

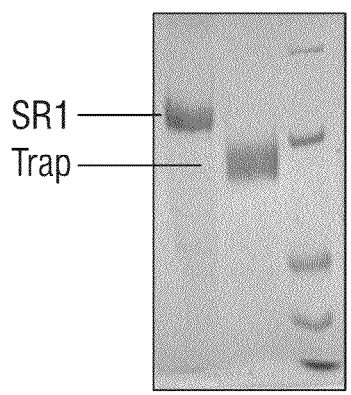
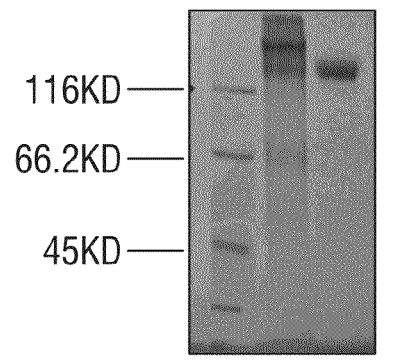
*FIG. 4A*
*FIG. 4B*
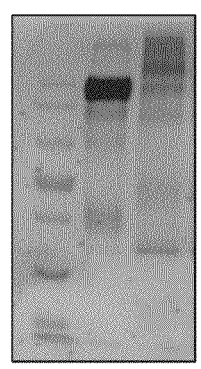
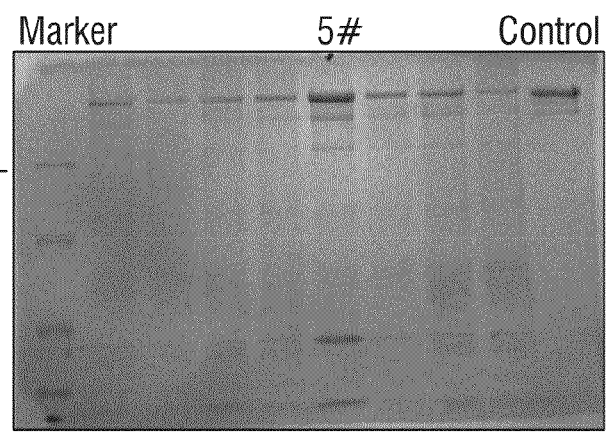
*FIG. 5*
*FIG. 6*

SR1 High-Dose Group

SR1 Low-Dose Group

Trap Control Group

PBS Negative Control Group

US 8,926,972 B2

SEQUENCE LISTING

```
<160> NUMBER OF SEQ ID NOS: 10

<210> SEQ ID NO 1
<211> LENGTH: 103
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(103)
<223> OTHER INFORMATION: immunoglobulin-like domain 2 amino acid
``` sequence of extracellular domain of Flt1 (Flt1D2)

<400> SEQUENCE: 1

Ser Asp Thr Gly Arg Pro Phe Val Glu Met Tyr Ser Glu Ile Pro Glu
 1               5                  10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                85                  90                  95

Gln Thr Asn Thr Ile Ile Asp
            100

<210> SEQ ID NO 2
<211> LENGTH: 204
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(204)
<223> OTHER INFORMATION: immunoglobulin-like domain 2 & 3 amino acid
      sequence of extracellular domain of KDR (KDRD2-KDRD3)

<400> SEQUENCE: 2

Pro Phe Ile Ala Ser Val Ser Asp Gln His Gly Val Val Tyr Ile Thr
 1               5                  10                  15

Glu Asn Lys Asn Lys Thr Val Val Ile Pro Cys Leu Gly Ser Ile Ser
            20                  25                  30

Asn Leu Asn Val Ser Leu Cys Ala Arg Tyr Pro Glu Lys Arg Phe Val
        35                  40                  45

Pro Asp Gly Asn Arg Ile Ser Trp Asp Ser Lys Lys Gly Phe Thr Ile
    50                  55                  60

Pro Ser Tyr Met Ile Ser Tyr Ala Gly Met Val Phe Cys Glu Ala Lys
 65                  70                  75                  80

Ile Asn Asp Glu Ser Tyr Gln Ser Ile Met Tyr Ile Val Val Val Val
                85                  90                  95

Gly Tyr Arg Ile Tyr Asp Val Val Leu Ser Pro Ser His Gly Ile Glu
            100                 105                 110

Leu Ser Val Gly Glu Lys Leu Val Leu Asn Cys Thr Ala Arg Thr Glu
        115                 120                 125

Leu Asn Val Gly Ile Asp Phe Asn Trp Glu Tyr Pro Ser Ser Lys His
    130                 135                 140

Gln His Lys Lys Leu Val Asn Arg Asp Leu Lys Thr Gln Ser Gly Ser
145                 150                 155                 160

Glu Met Lys Lys Phe Leu Ser Thr Leu Thr Ile Asp Gly Val Thr Arg
                165                 170                 175

Ser Asp Gln Gly Leu Tyr Thr Cys Ala Ala Ser Ser Gly Leu Met Thr
            180                 185                 190

Lys Lys Asn Ser Thr Phe Val Arg Val His Glu Lys
        195                 200

<210> SEQ ID NO 3
<211> LENGTH: 93
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(93)
<223> OTHER INFORMATION: immunoglobulin-like domain 4 amino acid
      sequence of extracellular domain of KDR (KDRD4)

<400> SEQUENCE: 3

Phe Val Ala Phe Gly Ser Gly Met Glu Ser Leu Val Glu Ala Thr Val
 1               5                  10                  15

Gly Glu Arg Val Arg Ile Pro Ala Lys Tyr Leu Gly Tyr Pro Pro Pro
             20                  25                  30

Glu Ile Lys Trp Tyr Lys Asn Gly Ile Pro Leu Glu Ser Asn His Thr
         35                  40                  45

Ile Lys Ala Gly His Val Leu Thr Ile Met Glu Val Ser Glu Arg Asp
     50                  55                  60

Thr Gly Asn Tyr Thr Val Ile Leu Thr Asn Pro Ile Ser Lys Glu Lys
 65                  70                  75                  80

Gln Ser His Val Val Ser Leu Val Val Tyr Val Pro Pro
                 85                  90

<210> SEQ ID NO 4
<211> LENGTH: 96
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(96)
<223> OTHER INFORMATION: immunoglobulin-like domain 4 amino acid
      sequence of extracellular domain of Flt1 (Flt1D4)

<400> SEQUENCE: 4

Phe Ile Thr Val Lys His Arg Lys Gln Gln Val Leu Glu Thr Val Ala
 1               5                  10                  15

Gly Lys Arg Ser Tyr Arg Leu Ser Met Lys Val Lys Ala Phe Pro Ser
             20                  25                  30

Pro Glu Val Val Trp Leu Lys Asp Gly Leu Pro Ala Thr Glu Lys Ser
         35                  40                  45

Ala Arg Tyr Leu Thr Arg Gly Tyr Ser Leu Ile Ile Lys Asp Val Thr
     50                  55                  60

Glu Glu Asp Ala Gly Asn Tyr Thr Ile Leu Leu Ser Ile Lys Gln Ser
 65                  70                  75                  80

Asn Val Phe Lys Asn Leu Thr Ala Thr Leu Ile Val Asn Val Lys Pro
                 85                  90                  95

<210> SEQ ID NO 5
<211> LENGTH: 195
<212> TYPE: PRT
<213> ORGANISM: Artificial Sequence
<220> FEATURE:
<223> OTHER INFORMATION: synthetic construct
<220> FEATURE:
<221> NAME/KEY: DOMAIN
<222> LOCATION: (1)...(195)
<223> OTHER INFORMATION: amino acid sequence of human IgG1Fc (IgGF1FC)

<400> SEQUENCE: 5

```
Ile Ser Arg Thr Pro Glu Val Thr Cys Val Val Val Asp Val Ser His
 1               5                  10                  15

Glu Asp Pro Glu Val Lys Phe Asn Trp Tyr Val Asp Gly Val Glu Val
            20                  25                  30

His Asn Ala Lys Thr Lys Pro Arg Glu Glu Gln Tyr Asn Ser Thr Tyr
        35                  40                  45

Arg Val Val Ser Val Leu Thr Val Leu His Gln Asp Trp Leu Asn Gly
    50                  55                  60

Lys Glu Tyr Lys Cys Lys Val Ser Asn Lys Ala Leu Pro Ala Pro Ile
 65                  70                  75                  80

Glu Lys Thr Ile Ser Lys Ala Lys Gly Gln Pro Arg Glu Pro Gln Val
                85                  90                  95

Tyr Thr Leu Pro Pro Ser Arg Asp Glu Leu Thr Lys Asn Gln Val Ser
            100                 105                 110

Leu Thr Cys Leu Val Lys Gly Phe Tyr Pro Ser Asp Ile Ala Val Glu
        115                 120                 125

Trp Glu Ser Asn Gly Gln Pro Glu Asn Asn Tyr Lys Thr Thr Pro Pro
    130                 135                 140

Val Leu Asp Ser Asp Gly Ser Phe Phe Leu Tyr Ser Lys Leu Thr Val
145                 150                 155                 160

Asp Lys Ser Arg Trp Gln Gln Gly Asn Val Phe Ser Cys Ser Val Met
                165                 170                 175

His Glu Ala Leu His Asn His Tyr Thr Gln Lys Ser Leu Ser Leu Ser
            180                 185                 190

Pro Gly Lys
        195

<210> SEQ ID NO 6
<211> LENGTH: 534
<212> TYPE: PRT
<213> ORGANISM: Artificial Sequence
<220> FEATURE:
<223> OTHER INFORMATION: synthetically constructed fusion protein SR1

<400> SEQUENCE: 6

Ser Asp Thr Gly Arg Pro Phe Val Glu Met Tyr Ser Glu Ile Pro Glu
 1               5                  10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                85                  90                  95

Gln Thr Asn Thr Ile Ile Asp Pro Phe Ile Ala Ser Val Ser Asp Gln
            100                 105                 110

His Gly Val Val Tyr Ile Thr Glu Asn Lys Asn Lys Thr Val Val Ile
        115                 120                 125

Pro Cys Leu Gly Ser Ile Ser Asn Leu Asn Val Ser Leu Cys Ala Arg
    130                 135                 140

Tyr Pro Glu Lys Arg Phe Val Pro Asp Gly Asn Arg Ile Ser Trp Asp
145                 150                 155                 160
```

-continued

```
Ser Lys Lys Gly Phe Thr Ile Pro Ser Tyr Met Ile Ser Tyr Ala Gly
                165                 170                 175

Met Val Phe Cys Glu Ala Lys Ile Asn Asp Glu Ser Tyr Gln Ser Ile
            180                 185                 190

Met Tyr Ile Val Val Val Gly Tyr Arg Ile Tyr Asp Val Val Leu
        195                 200                 205

Ser Pro Ser His Gly Ile Glu Leu Ser Val Gly Glu Lys Leu Val Leu
    210                 215                 220

Asn Cys Thr Ala Arg Thr Glu Leu Asn Val Gly Ile Asp Phe Asn Trp
225                 230                 235                 240

Glu Tyr Pro Ser Ser Lys His Gln His Lys Lys Leu Val Asn Arg Asp
                245                 250                 255

Leu Lys Thr Gln Ser Gly Ser Glu Met Lys Lys Phe Leu Ser Thr Leu
            260                 265                 270

Thr Ile Asp Gly Val Thr Arg Ser Asp Gln Gly Leu Tyr Thr Cys Ala
        275                 280                 285

Ala Ser Ser Gly Leu Met Thr Lys Lys Asn Ser Thr Phe Val Arg Val
    290                 295                 300

His Glu Lys Asp Lys Thr His Thr Cys Pro Pro Cys Pro Ala Pro Glu
305                 310                 315                 320

Leu Leu Gly Gly Pro Ser Val Phe Leu Phe Pro Pro Lys Pro Lys Asp
                325                 330                 335

Thr Leu Met Ile Ser Arg Thr Pro Glu Val Thr Cys Val Val Val Asp
            340                 345                 350

Val Ser His Glu Asp Pro Glu Val Lys Phe Asn Trp Tyr Val Asp Gly
        355                 360                 365

Val Glu Val His Asn Ala Lys Thr Lys Pro Arg Glu Glu Gln Tyr Asn
    370                 375                 380

Ser Thr Tyr Arg Val Val Ser Val Leu Thr Val Leu His Gln Asp Trp
385                 390                 395                 400

Leu Asn Gly Lys Glu Tyr Lys Cys Lys Val Ser Asn Lys Ala Leu Pro
                405                 410                 415

Ala Pro Ile Glu Lys Thr Ile Ser Lys Ala Lys Gly Gln Pro Arg Glu
            420                 425                 430

Pro Gln Val Tyr Thr Leu Pro Pro Ser Arg Asp Glu Leu Thr Lys Asn
        435                 440                 445

Gln Val Ser Leu Thr Cys Leu Val Lys Gly Phe Tyr Pro Ser Asp Ile
    450                 455                 460

Ser Leu Ala Val Glu Trp Glu Ser Asn Gly Gln Pro Glu Asn Asn Tyr
465                 470                 475                 480

Lys Thr Thr Pro Pro Val Leu Asp Ser Asp Gly Ser Phe Phe Leu Tyr
                485                 490                 495

Ser Lys Leu Thr Val Asp Lys Ser Arg Trp Gln Gln Gly Asn Val Phe
            500                 505                 510

Ser Cys Ser Val Met His Glu Ala Leu His Asn His Tyr Thr Gln Lys
        515                 520                 525

Ser Leu Ser Pro Gly Lys
    530

<210> SEQ ID NO 7
<211> LENGTH: 423
<212> TYPE: PRT
<213> ORGANISM: Artificial Sequence
<220> FEATURE:
```

<223> OTHER INFORMATION: synthetically constructed fusion protein SR2

<400> SEQUENCE: 7

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Phe Val Ala Phe Gly Ser Gly Met Glu
            100                 105                 110

Ser Leu Val Glu Ala Thr Val Gly Glu Arg Val Arg Ile Pro Ala Lys
        115                 120                 125

Tyr Leu Gly Tyr Pro Pro Glu Ile Lys Trp Tyr Lys Asn Gly Ile
    130                 135                 140

Pro Leu Glu Ser Asn His Thr Ile Lys Ala Gly His Val Leu Thr Ile
145                 150                 155                 160

Met Glu Val Ser Glu Arg Asp Thr Gly Asn Tyr Thr Val Ile Leu Thr
                165                 170                 175

Asn Pro Ile Ser Lys Glu Lys Gln Ser His Val Val Ser Leu Val Val
            180                 185                 190

Tyr Val Pro Pro Asp Lys Thr His Thr Cys Pro Pro Cys Pro Ala Pro
        195                 200                 205

Glu Leu Leu Gly Gly Pro Ser Val Phe Leu Phe Pro Pro Lys Pro Lys
    210                 215                 220

Asp Thr Leu Met Ile Ser Arg Thr Pro Glu Val Thr Cys Val Val Val
225                 230                 235                 240

Asp Val Ser His Glu Asp Pro Glu Val Lys Phe Asn Trp Tyr Val Asp
                245                 250                 255

Gly Val Glu Val His Asn Ala Lys Thr Lys Pro Arg Glu Glu Gln Tyr
            260                 265                 270

Asn Ser Thr Tyr Arg Val Val Ser Val Leu Thr Val Leu His Gln Asp
        275                 280                 285

Trp Leu Asn Gly Lys Glu Tyr Lys Cys Lys Val Ser Asn Lys Ala Leu
    290                 295                 300

Pro Ala Pro Ile Glu Lys Thr Ile Ser Lys Ala Lys Gly Gln Pro Arg
305                 310                 315                 320

Glu Pro Gln Val Tyr Thr Leu Pro Pro Ser Arg Asp Glu Leu Thr Lys
                325                 330                 335

Asn Gln Val Ser Leu Thr Cys Leu Val Lys Gly Phe Tyr Pro Ser Asp
            340                 345                 350

Ile Ala Val Glu Trp Glu Ser Asn Gly Gln Pro Glu Asn Asn Tyr Lys
        355                 360                 365

Thr Thr Pro Pro Val Leu Asp Ser Asp Gly Ser Phe Phe Leu Tyr Ser
    370                 375                 380

Lys Leu Thr Val Asp Lys Ser Arg Trp Gln Gln Gly Asn Val Phe Ser
385                 390                 395                 400
```

Cys Ser Val Met His Glu Ala Leu His Asn His Tyr Thr Gln Lys Ser
            405                 410                 415

Leu Ser Leu Ser Pro Gly Lys
            420

<210> SEQ ID NO 8
<211> LENGTH: 426
<212> TYPE: PRT
<213> ORGANISM: Artificial Sequence
<220> FEATURE:
<223> OTHER INFORMATION: synthetically constructed fusion protein SR3

<400> SEQUENCE: 8

Ser Asp Thr Gly Arg Pro Phe Val Glu Met Tyr Ser Glu Ile Pro Glu
 1               5                  10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Phe Ile Thr Val Lys His Arg Lys Gln
            100                 105                 110

Gln Val Leu Glu Thr Val Ala Gly Lys Arg Ser Tyr Arg Leu Ser Met
        115                 120                 125

Lys Val Lys Ala Phe Pro Ser Pro Glu Val Val Trp Leu Lys Asp Gly
130                 135                 140

Leu Pro Ala Thr Glu Lys Ser Ala Arg Tyr Leu Thr Arg Gly Tyr Ser
145                 150                 155                 160

Leu Ile Ile Lys Asp Val Thr Glu Glu Asp Ala Gly Asn Tyr Thr Ile
                165                 170                 175

Leu Leu Ser Ile Lys Gln Ser Asn Val Phe Lys Asn Leu Thr Ala Thr
            180                 185                 190

Leu Ile Val Asn Val Lys Pro Asp Lys Thr His Thr Cys Pro Pro Cys
        195                 200                 205

Pro Ala Pro Glu Leu Leu Gly Gly Pro Ser Val Phe Leu Phe Pro Pro
210                 215                 220

Lys Pro Lys Asp Thr Leu Met Ile Ser Arg Thr Pro Glu Val Thr Cys
225                 230                 235                 240

Val Val Val Asp Val Ser His Glu Asp Pro Glu Val Lys Phe Asn Trp
                245                 250                 255

Tyr Val Asp Gly Val Glu Val His Asn Ala Lys Thr Lys Pro Arg Glu
            260                 265                 270

Glu Gln Tyr Asn Ser Thr Tyr Arg Val Val Ser Val Leu Thr Val Leu
        275                 280                 285

His Gln Asp Trp Leu Asn Gly Lys Glu Tyr Lys Cys Lys Val Ser Asn
    290                 295                 300

Lys Ala Leu Pro Ala Pro Ile Glu Lys Thr Ile Ser Lys Ala Lys Gly
305                 310                 315                 320

Gln Pro Arg Glu Pro Gln Val Tyr Thr Leu Pro Pro Ser Arg Asp Glu
                325                 330                 335

-continued

```
Leu Thr Lys Asn Gln Val Ser Leu Thr Cys Leu Val Lys Gly Phe Tyr
                340                 345                 350

Pro Ser Asp Ile Ala Val Glu Trp Glu Ser Asn Gly Gln Pro Glu Asn
            355                 360                 365

Asn Tyr Lys Thr Thr Pro Pro Val Leu Asp Ser Asp Gly Ser Phe Phe
        370                 375                 380

Leu Tyr Ser Lys Leu Thr Val Asp Lys Ser Arg Trp Gln Gln Gly Asn
385                 390                 395                 400

Val Phe Ser Cys Ser Val Met His Glu Ala Leu His Asn His Tyr Thr
                405                 410                 415

Gln Lys Ser Leu Ser Leu Ser Pro Gly Lys
            420                 425
```

<210> SEQ ID NO 9
<211> LENGTH: 763
<212> TYPE: PRT
<213> ORGANISM: Homo sapiens
<220> FEATURE:
<221> NAME/KEY: DOMAIN
<222> LOCATION: (1)...(763)
<223> OTHER INFORMATION: Flt 1 protein

<400> SEQUENCE: 9

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
```

```
                    260                 265                 270
Asn Lys Arg Ala Ser Val Arg Arg Ile Asp Gln Ser Asn Ser His
            275                 280                 285
Ala Asn Ile Phe Tyr Ser Val Leu Thr Ile Asp Lys Met Gln Asn Lys
        290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
        355                 360                 365
Trp Leu Lys Asp Gly Leu Pro Ala Thr Glu Lys Ser Ala Arg Tyr Leu
    370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
        435                 440                 445
Arg Gln Ile Leu Thr Cys Thr Ala Tyr Gly Ile Pro Gln Pro Thr Ile
    450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
    530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
    610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
            660                 665                 670
Ala Ile Ser Ser Ser Thr Thr Leu Asp Cys His Ala Asn Gly Val Pro
        675                 680                 685
```

-continued

```
Glu Pro Gln Ile Thr Trp Phe Lys Asn Asn His Lys Ile Gln Gln Glu
            690             695                 700
Pro Gly Ile Ile Leu Gly Pro Gly Ser Ser Thr Leu Phe Ile Glu Arg
705             710                 715                 720
Val Thr Glu Glu Asp Glu Gly Val Tyr His Cys Lys Ala Thr Asn Gln
                725                 730                 735
Lys Gly Ser Val Glu Ser Ser Ala Tyr Leu Thr Val Gln Gly Thr Ser
            740                 745                 750
Asp Lys Ser Asn Leu Glu Leu Ile Thr Leu Thr
            755                 760

<210> SEQ ID NO 10
<211> LENGTH: 762
<212> TYPE: PRT
<213> ORGANISM: Homo sapiens
<220> FEATURE:
<221> NAME/KEY: DOMAIN
<222> LOCATION: (1)...(762)
<223> OTHER INFORMATION: KDR protein

<400> SEQUENCE: 10

Met Gln Ser Lys Val Leu Leu Ala Val Ala Leu Trp Leu Cys Val Glu
  1               5                  10                  15
Thr Arg Ala Ala Ser Val Gly Leu Pro Ser Val Ser Leu Asp Leu Pro
             20                  25                  30
Arg Leu Ser Ile Gln Lys Asp Ile Leu Thr Ile Lys Ala Asn Thr Thr
         35                  40                  45
Leu Gln Ile Thr Cys Arg Gly Gln Arg Asp Leu Asp Trp Leu Trp Pro
 50                  55                  60
Asn Asn Gln Ser Gly Ser Glu Gln Arg Val Glu Val Thr Glu Cys Ser
65                  70                  75                  80
Asp Gly Leu Phe Cys Lys Thr Leu Thr Ile Pro Lys Val Ile Gly Asn
                 85                  90                  95
Asp Thr Gly Ala Tyr Lys Cys Phe Tyr Arg Glu Thr Asp Leu Ala Ser
            100                 105                 110
Val Ile Tyr Val Tyr Val Gln Asp Tyr Arg Ser Pro Phe Ile Ala Ser
        115                 120                 125
Val Ser Asp Gln His Gly Val Val Tyr Ile Thr Glu Asn Lys Asn Lys
130                 135                 140
Thr Val Val Ile Pro Cys Leu Gly Ser Ile Ser Asn Leu Asn Val Ser
145                 150                 155                 160
Leu Cys Ala Arg Tyr Pro Glu Lys Arg Phe Val Pro Asp Gly Asn Arg
                165                 170                 175
Ile Ser Trp Asp Ser Lys Lys Gly Phe Thr Ile Pro Ser Tyr Met Ile
            180                 185                 190
Ser Tyr Ala Gly Met Val Phe Cys Glu Ala Lys Ile Asn Asp Glu Ser
        195                 200                 205
Tyr Gln Ser Ile Met Tyr Ile Val Val Val Gly Tyr Arg Ile Tyr
    210                 215                 220
Asp Val Val Leu Ser Pro Ser His Gly Ile Glu Leu Ser Val Gly Glu
225                 230                 235                 240
Lys Leu Val Leu Asn Cys Thr Ala Arg Thr Glu Leu Asn Val Gly Ile
                245                 250                 255
Asp Phe Asn Trp Glu Tyr Pro Ser Ser Lys His Gln His Lys Lys Leu
            260                 265                 270
```

```
Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Glu Ile Lys Trp Tyr Lys Asn Gly
            355                 360                 365

Ile Pro Leu Glu Ser Asn His Thr Ile Lys Ala Gly His Val Leu Thr
            370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
            435                 440                 445

Ala Ile Pro Pro Pro His His Ile His Trp Tyr Trp Gln Leu Glu Glu
            450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
            595                 600                 605

Leu Trp Lys Leu Asn Ala Thr Met Phe Ser Asn Ser Thr Asn Asp Ile
            610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
```

|  |  |  | 690 |  |  |  | 695 |  |  |  | 700 |  |
|---|---|---|---|---|---|---|---|---|---|---|---|---|

Glu Thr Leu Val Glu Asp Ser Gly Ile Val Leu Lys Asp Gly Asn Arg
705                  710                715                720

Asn Leu Thr Ile Arg Arg Val Arg Lys Glu Asp Glu Gly Leu Tyr Thr
            725                 730                735

Cys Gln Ala Cys Ser Val Leu Gly Cys Ala Lys Val Glu Ala Phe Phe
            740                 745                750

Ile Ile Glu Gly Ala Gln Glu Lys Thr Asn
        755                 760

ANTI-ANGIOGENESIS FUSION PROTEINS

CROSS-REFERENCE TO RELATED APPLICATIONS

This application claims the benefit of Chinese Patent Application No. 200910056955.8, filed on Mar. 18, 2009, U.S. Provisional Application No. 61/163,203, entitled "Anti-Angiogenesis Fusion Proteins," filed on Mar. 25, 2009, and PCT Application No. PCT/CN2010/071125 entitled "Anti-Angiogenesis Fusion Proteins," filed on Mar. 18, 2010, which applications are incorporated herein by reference in their entireties.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 655982000200Seqlist.txt | Jul. 13, 2010 | 31,924 bytes |

TECHNICAL FIELD

The present invention relates generally to the field of genetic engineering. More specifically, the present invention relates to recombinant DNA sequences, fusion proteins expressed from these DNA sequences and their use as medications to treat pathologic angiogenesis diseases.

BACKGROUND ART

The vasculature of a normal adult is generally quiescent, with endothelial cells dividing approximately every 10 years; the formation of new blood vessels (angiogenesis) occurs only in a few physiological and pathological circumstances. In physiological circumstances, angiogenesis occurs during wound healing, organ regeneration, and in the female reproductive system during ovulation, menstruation, and the formation of the placenta. Angiogenesis occurs under pathological circumstances such as tumor, rheumatoid arthritis, diabetic retinopathy, psoriasis, and age-related macular degeneration (AMD). Recent evidence suggest that angiogenesis is the lifeline of solid tumor growth and metastasis. (Hanahan and Folkman, Cell 1996, 86:353-364.) Thus, anti-angiogenic therapy has become a hotly pursued field for the treatment of cancer and other disease related to angiogenesis.

Angiogenesis is subject to a complex control system consisting of multiple pro-angiogenic and anti-angiogenic factors. In adults, angiogenesis is tightly controlled by the balance between these factors. Vascular endothelial growth factor (VEGF) is an important pro-angiogenic factor, which regulates endothelial proliferation, permeability, and survival with high efficacy and specificity. (Folkman et al., Science 1987, 235:442; Giampietro et al., Cancer Metastasis Rev. 1994; Ferrara, Endocrine Rev. 2004, 25(4):581-611.) Thus VEGF and its signally pathway have become important targets for anti-angiogenic therapy in pathological conditions such as solid tumors, rheumatoid arthritis, etc.

There are three VEGF receptors, VEGFR-1 (fms-like tyrosine kinase, Ht-1), VEGFR-2 (fetal liver kinase 1-murine homologue/Kinase insert Domain containing Receptor-human homologue, KDR/Flk-1), and VEGFR-3 (Flt-4). VEGFR-1 and VEGFR-2 are expressed primarily on endothelial cells. VEGFR-3 is mainly expressed on lymphatic vessels and neuropilin, and is also expressed on neuronal cells. Each receptor has seven immunoglobulin-like domains in the extracellular domain, a single transmembrane region, and a consensus tyrosine kinase sequence. The receptor undergoes dimerization and ligand-dependent tyrosine phosphorylation in intact cells and results in a mitogenic, chemotactic and prosurvival signal. It has been demonstrated that VEGFR-2 is the major mediator of vascular endothelial cells (EC) mitogenesis and survival, as well as angiogenesis and microvascular permeability. (Ferrara N. et al., Nature Medicine 2003, 9(6):669-676.)

Blocking antibodies against VEGF or soluble VEGF receptor fragments can inhibit the binding of VEGF to VEGF receptors on vascular endothelial cells, thus block the VEGF-initiated signal transduction, and the pathological angiogenesis resulting from high VEGF expression. These angiogenesis inhibitors that have been developed as therapeutics include bevacizumab (Avastin), Lucentis, VEGF-Trap, etc. to treat angiogenesis-related diseases. Current anti-angiogenic drug Avastin of Genentech approved by FDA in 2004 is an example of specific anti-VEGF monoclonal antibody. (Ferrara et al., Nature Rev. Drug Disc. 2004, 3:391-400.) Its therapeutic mechanism is blocking VEGF-VEGF receptor interaction through binding to the VEGF molecule. However, it has two disadvantages: 1) relatively low binding affinity $2.3 \times 10^{-9}$ leading to large doses; and 2) without inhibitory effect on placental growth factor (PIGF).

U.S. Pat. Nos. 6,100,071 and 5,952,199 describe VEGF binding fusion protein with Flt1 and KDR fragments, but these fusion proteins were not further developed because of low stability and serious side-effects. Although a fragment of Flt1 extracellular domain spanning the $2^{nd}$ and $3^{rd}$ immunoglobulin-like domains contains most of its binding activity to VEGF and PIGF, it has low effective activity in vivo because of its consecutive basic amino acids in the third immunoglobulin-like domain. Further, some therapeutics undergoing clinical trials, e.g., VEGF-Trap from Regeneron, have a stoichiometric ratio of 1:1 to VEGF molecules.

The present invention not only retains the binding activity of human Flt1 and KDR to VEGF and the binding activity to PIGF, but also provides enhanced bivalent interaction because of the increased distance between the two VEGF-binding immunoglobulin-like domains.

SUMMARY OF THE INVENTION

The present invention is directed at chimeric and/or humanized anti-angiogenesis fusion proteins, and their therapeutic use for treatment of angiogenesis-related diseases.

In one aspect, the present invention provides a fusion protein comprising a chimeric VEGF receptor or a fragment thereof and a multimerizing component, wherein the chimeric VEGF receptor or the fragment thereof comprises amino acid sequences from two different VEGF receptors, and the fusion protein binds with high affinity to VEGF. In one embodiment, the chimeric VEGF receptor or fragment thereof comprises amino acid sequences from three different VEGF receptors. In another embodiment, the fusion protein is a recombinant fusion protein. In some embodiments, the fusion protein binds with high affinity to placental growth factor (PIGF).

The VEGF receptor may be from multiple species or from a single species. In one embodiment, the VEGF receptor is a human VEGF receptor. In another embodiment, the VEGF receptor is selected from the group consisting of Flt1, KDR and Flt4. In yet another embodiment, the chimeric VEGF receptor fragment comprises an extracellular domain of the VEGF receptor. In still another embodiment, the extracellular domain of the VEGF receptor comprises an immunoglobulin-like domain of the VEGF receptor.

The immunoglobulin-like domain of the VEGF receptor may be the immunoglobulin-like domain 2 of the extracellular domain of Flt1 (Flt1D2), the immunoglobulin-like domain 4 of the extracellular domain of Flt1 (Flt1D4), the immunoglobulin-like domain 2 of the extracellular domain of KDR (KDRD2), the immunoglobulin-like domain 3 of the extracellular domain of KDR (KDRD3), or the immunoglobulin-like domain 4 of the extracellular domain of KDR (KDRD4). In one embodiment, the extracellular domain of the VEGF receptor comprises Flt1D2-KDRD2-KDRD3. In another embodiment, the extracellular domain of the VEGF receptor comprises Flt1D2-KDRD4. In yet another embodiment, the extracellular domain of the VEGF receptor comprises Flt1D2-Flt1D4.

The multimerizing component may comprise an Fc fragment of human immunoglobulin. In one embodiment, the human immunoglobulin is selected from the group consisting of IgG, IgM and IgA. In another embodiment, the IgG is selected from the group consisting of IgG1, IgG2, IgG3 and IgG4. In some embodiments, the fusion protein may comprises the amino acid sequence set forth in SEQ ID NO:1-3 or a sequence substantially homologous thereto. In preferred embodiments, the chimeric VEGF receptor fragment is not Flt1D2-KDRD3.

Also provided herein is a pharmaceutical composition comprising a fusion protein comprising a chimeric VEGF receptor or a fragment thereof and a multimerizing component, wherein the chimeric VEGF receptor or the fragment thereof comprises amino acid sequences from two different VEGF receptors, and the fusion protein binds with high affinity to VEGF, and a pharmaceutically acceptable carrier, adjuvant or diluent. Further provided herein is a method of making a pharmaceutical composition for anti-angiogenesis, treating a VEGF-related disease or inhibiting tumor growth, which method comprises mixing the fusion protein with a pharmaceutically acceptable carrier, adjuvant or diluent. A kit comprising the fusion protein or the pharmaceutical composition is also provided.

In another aspect, the present invention provides a nucleic acid that encodes a fusion protein comprising a chimeric VEGF receptor or a fragment thereof and a multimerizing component, wherein the chimeric VEGF receptor or the fragment thereof comprises amino acid sequences from two different VEGF receptors, and the fusion protein binds with high affinity to VEGF. In one embodiment, the nucleic acid may be a recombinant DNA molecule. Also provided herein is a vector comprising the recombinant DNA molecule.

For recombinant production of the fusion protein, a wide variety of expression vectors can be constructed based on common molecular cloning protocols. The vector components generally include, but are not limited to, one or more of the following: a signal sequence for the secretion of expressed proteins, one or more marker genes including the selection marker gene for the stable cell line screening in eukaryote cells, an origin of replication, an enhancer element, a promoter, a transcription termination sequence, a poly A signal, an insulator, etc.

The expression vector may be constructed in a variety of ways. In one embodiment, the C-terminus of the chimeric VEGF receptor or a fragment thereof may be fused with the N-terminus of the IgG Fc fragment. In another embodiment, the N-terminus of the chimeric VEGF receptor or a fragment thereof may be fused with the C-terminus of the IgG Fc fragment. In yet another embodiment, a linker sequence may be introduced between the chimeric VEGF receptor or a fragment thereof and the IgG Fc fragment. In some embodiments, a linker sequence may be introduced between the immunoglobulin-like domains of the chimeric VEGF receptor or a fragment thereof.

Further provided in the present invention is a cell line transfected with the recombinant DNA molecule that encodes a fusion protein comprising a chimeric VEGF receptor or a fragment thereof and a multimerizing component, wherein the chimeric VEGF receptor or the fragment thereof comprises amino acid sequences from two different VEGF receptors, and the fusion protein binds with high affinity to VEGF. Transfection of the cell line may be stable or transient, and may be effected through electroporation or liposome-mediated methods.

The host cells for expression of the vector encoding the fusion polypeptide include (but not limited in) prokaryotic, yeast, insect, or higher eukaryotic cells, etc. In one embodiment, mammalian cell lines that are used to produce the fusion polypeptide may include: 293, CHO, sp2/0, NS0, COS, BHK, and PER.C6, among others.

Also provided in the present invention is a method of producing a fusion protein comprising a chimeric VEGF receptor or a fragment thereof and a multimerizing component, wherein the chimeric VEGF receptor or the fragment thereof comprises amino acid sequences from two different VEGF receptors, and the fusion protein binds with high affinity to VEGF, comprising culturing the cell line transfected with the recombinant DNA molecule that encodes the fusion protein, and recovering the fusion protein expressed thereby. In one embodiment, the fusion protein can be purified by protein A affinity chromatography. In another embodiment, the purified fusion polypeptide may be glycosylated.

In a further aspect, the present invention provides a composition, which composition comprises: a) a fusion protein comprising a chimeric VEGF receptor or a fragment thereof and a multimerizing component; and b) a PlGF molecule, wherein the fusion protein binds with high affinity to the PlGF molecule. In one embodiment, the fusion protein binds to the PlGF molecule through the chimeric VEGF receptor or fragment thereof. In another embodiment, the chimeric VEGF receptor or fragment thereof binds to the PlGF molecule bivalently or multivalently.

In still a further aspect, the present invention provides a method for anti-angiogenesis, treating a VEGF-related disease or inhibiting tumor growth, which method comprises administrating to a subject an effective amount of the pharmaceutical composition comprising a fusion protein comprising a chimeric VEGF receptor or a fragment thereof and a multimerizing component, wherein the chimeric VEGF receptor or the fragment thereof comprises amino acid sequences from two different VEGF receptors, and the fusion protein binds with high affinity to VEGF, and a pharmaceutically acceptable carrier, adjuvant or diluent.

BRIEF DESCRIPTION OF THE DRAWINGS

FIGS. 1A-B show the domain structure of the extracellular domain of Flt1 (SEQ ID NO:9) and KDR (SEQ ID NO:10).

FIGS. 4A-B show the results from denaturing and non-denaturing SDS-PAGE analysis of transiently transfected fusion protein SR1.

FIG. 5 shows the results from Western blot analysis of transiently transfected fusion protein SR1.

FIG. 6 shows the results from non-denaturing SDS-PAGE of the fusion protein SR1 expressed in clone #5.

DETAILED DESCRIPTION OF THE INVENTION

Figure 2:
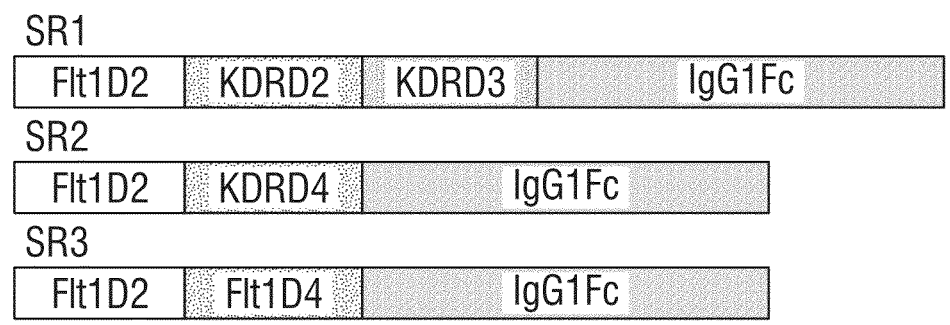
FIG. 2 shows the schematic profile of fusion proteins SR1, SR2 and SR3.

A desirable VEGF inhibitor is the extracellular domain of VEGF receptors, which naturally have high affinity (20-100 times higher than Avastin) and specificity to VEGF. (Kuo et al., Proceedings of the National Academy of Sciences 2001, 98:4605-4610; Ferrara N. et al., Nature Medicine 2003, 9(6): 669-676.) Recent study revealed that anti-PlGF antibodies inhibited tumor angiogenesis and metastasis, and enhanced the anti-angiogenic therapeutic efficacy of anti-VEGF antibodies. Furthermore, anti-PlGF antibodies inhibited growth of tumors which were resistant to anti-VEGF antibodies. (Fischer C. et al., Cell 2007, 131:463-475). Therefore, fusion proteins with an extracellular domain of Flt-1 having high affinity to PlGF combine the anti-angiogenic effects of anti-VEGF and anti-PlGF antibodies and are more effective as anti-angiogenic therapeutics. (Christinger et al., J. Biol. Chem. 2004, 279(11):10382-10388.)

Fc-fusion proteins are a group of recombinant proteins which is composed of the hinge region, CH2 domain and CH3 domain of immunoglobulin heavy chain (the Fc fragment) and the biologically active proteins or biological active domains of proteins. This type of fusion polypeptides possesses the following characters: it reserves the biological activity of the fused protein or protein domain; it directs the Fc fragment of the fusion polypeptide to the particular cells via the reaction of the biologically active protein or protein domain to the target protein and functions of the Fc fragment, such as antibody-dependent cell-mediated cytotoxicity (ADCC), immunoregulation, etc.; its extends the half-life of the fusion polypeptide in vivo as well as its pharmaceutical effect; purification of Fc-fusion polypeptide becomes relatively fast and easy because of the binding ability of the Fc fragment to Protein A; and Fc fragment forms dimers which gives the fusion polypeptide stronger binding ability to the target protein. A lot of proteins can be fused to an Fc fragment, several Fc-fusion polypeptides such as ENBREL®, VEGF Trap are widely used in clinical settings to combat malignant tumor, autoimmune disease and infection with excellent results.

The present invention relates generally to a fusion protein comprising a chimeric VEGF receptor or a fragment thereof and a multimerizing component, wherein the chimeric VEGF receptor or the fragment thereof comprises amino acid sequences from two different VEGF receptors, and the fusion protein binds with high affinity to VEGF. The chimeric VEGF receptor or fragment thereof may comprise the immunoglobulin-like domains from multiple VEGF receptors from different or same species. The multimerizing component may comprise an Fc fragment of a human immunoglobulin. The Fc-fusion polypeptide described in the present invention may also bind with high affinity to a PlGF. A major advantage of the present invention is the ability to bind VEGF and PlGF molecules multivalently because of the greater distance between the immunoglobulin like domains of the fusion protein.

Definitions

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular form "a", "an", and "the" include plural references unless indicated otherwise. For example, "a" dimer includes one of more dimers.

As used herein, "Flt1," "Flt-1," and "VEGFR-1" can be used interchangeably. They all refer to VEGF Receptor 1.

As used herein, "Flk-1," "KDR," and "VEGFR-2" can be used interchangeably. They all refer to VEGF Receptor 2.

As used herein, a "polypeptide" includes proteins, fragments of proteins, and peptides, whether isolated from natural sources, produced by recombinant techniques, or chemically synthesized. A polypeptide may have one or more modifications, such as a post-translational modification (e.g., glycosylation, etc.) or any other modification (e.g., pegylation, etc.). The polypeptide may contain one or more non-naturally-occurring amino acids (e.g., such as an amino acid with a side chain modification). Polypeptides of the invention typically comprise at least about 10 amino acids.

As used herein, "binds to" refers to the interaction of the fusion protein with the VEGF or PlGF molecule, which is typically a non-covalent or covalent interaction. The interaction of the fusion protein with the VEGF or PlGF molecule can be characterized in terms of a binding affinity. Binding affinity can be readily determined using standard technology. For example, the BIAcore™ system (Uppsala, Sweden) is one method for determining binding affinity. The BIAcore™ system uses surface plasmon resonance (S P R, Welford K. 1991, Opt. Quant. Elect. 23:1; Morton and Myszka, 1998, Methods in Enzymology 295: 268) to monitor biomolecular interactions in real time. BIAcore™ analysis conveniently generates association rate constants, dissociation rate constants, equilibrium dissociation constants, stoichiometry of interation, and affinity constants. An interaction between the fusion protein and a VEGF or PlGF molecule with "high affinity" may refer to an interaction with an $EC_{50}$ of lower than 10 µg/ml, 1 µg/ml, 0.5 µg/ml, 0.1 µg/ml, or 0.01 µg/ml.

An interaction between the fusion protein and a VEGF or PlGF molecule with high affinity may also refer to an interaction with a stoichiometry of greater than 1:1, for example, 1.1:1, 1.2:1, 1.5:1, 2:1, 3:1, or 5:1.

A "biologically active" polypeptide is an entity having any function related to or associated with a metabolic or physiological process, and/or having structural, regulatory, or biochemical functions of a naturally-occurring molecule. A biologically active polypeptide or fragment thereof includes one that can participate in a biological reaction, including, but not limited to, a ligand-receptor interaction or antigen-antibody binding. The biological activity can include an improved desired activity, or a decreased undesirable activity.

As used herein, an "Fc fragment" or "Fc region" refers to the tail region of an antibody that interacts with cell surface receptors called Fc receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains (CH domains 2-4) in each polypeptide chain. Typically, the common structural features for Fc fragments from different classes of immunoglobulins are a hinge region, a CH2 domain and a CH3 domain.

As used herein, an "extracellular domain" is the portion of the cell surface receptor that occurs on the surface of the receptor and includes the ligand binding site(s). For purposes herein, reference to an extracellular domain includes any extracellular domain-containing molecule, or portion thereof, so long as the extracellular domain polypeptide does not contain any contiguous sequence associated with another domain (i.e. transmembrante, protein kinase domain, or others) of a cognate receptor. Thus, for example, an extracellular domain polypeptide includes alternative spliced isoforms of cell surface receptors where the isoform has an extracellular domain-containing portion, but lacks any other domains of a cognate cell surface receptor, and also has additional sequences not associated or aligned with another domain sequence of a cognate cell surface receptor. These additional sequences can be intron-encoded sequences such as occur in intron fusion protein isoforms. Typically, the additional sequences do not inhibit or interfere with the ligand binding and/or receptor dimerization activities of a cell surface receptor extracellular domain polypeptide. An extracellular domain polypeptide also includes hybrid extracellular domains.

The terms "homologous", "substantially homologous", and "substantial homology" as used herein denote a sequence of amino acids having at least 50%, 60%, 70%, 80% or 90% identity wherein one sequence is compared to a reference sequence of amino acids. The percentage of sequence identity or homology is calculated by comparing one to another when aligned to corresponding portions of the reference sequence.

As used herein, a "reference" value can be an absolute value, a relative value, a value that has an upper or lower limit, a range of values, an average value, a median value, a mean value, or a value as compared to a particular control or baseline value.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, J. Biol. Chem., 266: 19867-19870 (1991)) can be inserted immediately 5' of the start codon and may enhance expression. The desirability of (or need for) such modification may be empirically determined.

As used herein, a "subject," "individual," "participant" or "patient" refers to any subject in need of diagnosis or treatment, preferably a mammal, and most preferably a human being. Other subjects include bovine, dog, cat, *Cavia porcellus*, rabbit, rat, mouse, horse, etc.

A "pharmaceutically acceptable carrier" refers to a non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Fusion Proteins

The amino acid sequences of Flt1 and KDR can be collected from public data bases. Because there is no distinct boundary between the immunoglobulin like domain of Flt1 and KDR, the amino acid sequence length of immunoglobulin-like domains can be varied. Therefore, the amino acid sequence of this disclosure may have some variation. All the variations are encompassed by this disclosure, including insertions, deletions, point mutations, etc.

Flt1D2 (SEQ ID NO:1) represents the immunoglobulin like-domain 2 amino acid sequence of the extracellular domain of Flt1. Flt1D4 (SEQ ID NO:4) represents the immunoglobulin-like domain 4 amino acid sequence of the extracellular domain of Flt1. KDRD2 represents the immunoglobulin-like domain 2 amino acid sequence of the extracellular domain of KDR. KDRD3 represents the immunoglobulin-like domain 3 amino acid sequence of the extracellular domain of KDR. KDRD4 (SEQ ID NO:3) represents the immunoglobulin-like domain 4 amino acid sequence of the extracellular domain of KDR.

The published literature shows that the second domain of Flt1 at N-terminus (Flt1D2) and the third domain of KDR at N-terminus (KDRD3) are the binding areas with VEGF, respectively. The third domain of Flt1 at N-terminus (Flt1D3) and the second domain of KDR at N-terminus (KDRD2) have very important role for the VEGF binding affinity, respectively.

The multimerizing component, usually as but not limited to Fc fragment of human immunoglobulin is encompassed by this disclosure. Human immunoglobulins include IgG, IgM, IgA or subclass IgG1, IgG2, IgG3, IgG4. The VEGF receptor or fragment may be and a single Fc fragment, or may have increased half-life in vivo because of dimerization between two Fc fragments.

A biologically active polypeptide or fragment thereof includes one that can participate in a biological reaction, including, but not limited to, a ligand-receptor interaction or antigen-antibody binding. Here, the VEGF receptor or the multimerizing component refers to a biologically active peptide which retains the respective VEGF-binding and multimerizing activities (at least 50%, 60%, 70%, 80%, and 90%). The VEGF receptor or multimerizing component disclosed in the present invention also includes polypeptides having amino acid changes such as substitution, deletion or insertion of one or more (e.g., 1-20, preferably 1-10, most preferably 1-5) amino acids. The fusion protein having a VEGF receptor or fragment having amino acid changes such as substitution, deletion or insertion of one or more amino acid retains the binding activity to VEGF. The present invention also includes modified or improved polypeptides, e.g., modified polypeptides with prolonged the half-life or increased stability.

In some embodiments, the human Fc domain fusion partner comprises the entire Fc domain. In some embodiments, it comprises one or more fragments of the Fc domain. In some embodiments, the fusion protein comprising the Fc polypeptide has reduced or lacks one or more effector functions. Naturally occurring IgG Fc region in the context of a fusion protein may lack the effector function(s) that the same sequence would have if it is in the context of a full-length antibody.

The VEGF receptor or fragment thereof can be directly linked to the multimerizing component, or through a peptide linker. The immunoglobulin-like domains of the chimeric VEGF receptor or fragment thereof can also be directly linked or linked through a peptide linker. The peptide linker may contain 0-20 amino acids, preferably 0-15 amino acids, more preferably 0-10 amino acids. Most preferably, the peptide linker may contain 1, 2, 3 or 4 amino acids. In a favored embodiment, the chimeric VEGF receptor or fragment thereof is directly linked to the multimerizing component, and so are the immunoglobulin-like domains.

Further, alternatively, the fusion protein may have one or more peptide tags at the N- or C-terminus. Any tags known in the art may be used in this invention. For example, the tag may be FLAG, HA, HAL c-Myc, 6-His, etc. These tags may be used for the purification of the fusion protein. In one embodiment, the fusion protein contains a 6-His tag at the C-terminus. As persons skilled in the art would know, an enzyme cleavage site may be included between the fusion protein and the peptide tag, so that the peptide tag can be removed from the fusion protein.

Nucleic Acids Encoding Fc-Fusion Polypeptides

In another aspect, the present invention provides a nucleic acid that encodes the recombinant fusion polypeptide, comprising a biologically active polypeptide linked to a human IgG2 Fc fragment, wherein said fusion polypeptide has a reduced amount of protein aggregate when produced in an expression system.

The nucleic acid may be naturally occurring nucleic acids DNA, RNA, or artificial nucleic acids including peptide nucleic acid (PNA), Morpholino and locked nucleic acid (LNA), as well as glycol nucleic acid (GNA) and threose nucleic acid (TNA). Both single-stranded and double-stranded nucleic acids may be used for the present invention. In some embodiments, the nucleic acid is a recombinant DNA molecule.

As used herein, "operatively linked" or "linked operatively" refer to the situation in which part of a linear DNA sequence can influence the other parts of the same DNA molecule. For example, when a promoter controls the transcription of the coding sequence, it is operatively linked to the coding sequence.

The invention also provides genetically engineered recombinant vectors comprising nucleic acid molecules encoding the fusion polypeptides of the invention. Vectors of the invention include those that are suitable for expression in a selected host, whether prokaryotic or eukaryotic, for example, phage, plasmid, and viral vectors. Viral vectors may be either replication competent or replication defective retroviral vectors. Viral propagation generally will occur only in complementing host cells comprising replication defective vectors. Vectors of the invention may comprise Kozak sequences (Lodish et al., Molecular Cell Biology, $4^{th}$ ed., 1999) and may also contain the ATG start codon. Promoters that function in an eukaryotic host include SV40, LTR, CMV, EF-1α, white cloud mountain minnow β-actin promoter, etc.

Copy number and positional effects are considered in designing transiently and stably expressed vectors. Copy number can be increased by, for example, dihydrofolate reductase amplification. Positional effects can be optimized by, for example, Chinese hamster elongation factor-1 vector pDEF38 (CHEF1), ubiquitous chromatin opening elements (UCOE), scaffold/matrix-attached region of human (S/MAR), and artificial chromosome expression (ACE) vectors, as well as by using site-specific integration methods known in the art. The expression constructs containing the vector and gene of interest will further contain sites for transcription initiation, termination, and, in the transcribed region, a ribosome binding site for translation. The coding portion of the transcripts expressed by the constructs can include a translation initiating codon at the beginning and a termination codon (UAA, UGA, or UAG) appropriately positioned at the end of the polypeptide to be translated.

Considering the above-mentioned factors, vectors suitable for expressing Fc-fusion polypeptides in bacteria include pTT vectors, available from Biotechnology Research Institute (Montreal, Canada), pQE70, pQE60, and pQE-9, available from Qiagen (Mississauga, Ontario, Canada); vectors derived from pcDNA3, available from Invitrogen (Carlsbad, Calif.); pBS vectors, Phagescript vectors, Bluescript vectors, pNH8A, pNH6a, pNH18A, pNH46A, available from Stratagene (La Jolla, Calif.); and ptrc99a, pKK223-3, pKK233-3, pDR540, pRIT5 available from Pharmacia (Peapack, N.J.). Among suitable eukaryotic vectors are pWLNEO, pSV2CAT, pOG44, pXT1, and pSG available from Stratagene (La Jolla, Calif.); and pSVK3, pBPV, pMSG and pSVL, available from Pharmacia (Peapack, N.J.).

Vectors for expressing Fc-fusion polypeptides include those comprising a pTT vector backbone (Durocher et al., Nucl. Acids Res. 30:E9 (2002)). Briefly, the backbone of a pTT vector may be prepared by obtaining pIRESpuro/EGFP (pEGFP) and pSEAP basic vector(s), for example from Clontech (Palo Alto, Calif.), and pcDNA3.1, pcDNA3.1/Myc-(His)6 and pCEP4 vectors can be obtained from, for example, Invitrogen (Carlsbad, Calif.). As used herein, the pTT5 backbone vector can generate a pTT5-Gateway vector and be used to transiently express proteins in mammalian cells. The pTT5 vector can be derivatized to pTT5-A, pTT5-B, pTT5-D, pTT5-E, pTT5-H, and pTT5-I, for example. As used herein, the pTT2 vector can generate constructs for stable expression in mammalian cell lines.

A pTT vector can be prepared by deleting the hygromycin (BsmI and SalI excision followed by fill-in and ligation) and EBNA1 (ClaI and NsiI excision followed by fill-in and ligation) expression cassettes. The ColEI origin (FspI-SalI fragment, including the 3' end of the β-lactamase open reading frame (ORF) can be replaced with a FspI-SalI fragment from pcDNA3.1 containing the pMBI origin (and the same 3' end of β-lactamase ORF). A Myc-(His)6 C-terminal fusion tag can be added to SEAP (HindIII-HpaI fragment from pSEAP-basic) following in-frame ligation in pcDNA3.1/Myc-His digested with HindIII and EcoRV. Plasmids can subsequently be amplified in *E. coli* (DH5α) grown in LB medium and purified using MAXI prep columns (Qiagen, Mississauga, Ontario, Canada). To quantify, plasmids can be subsequently diluted in, for example, 50 mM Tris-HCl pH 7.4 and absorbencies can be measured at 260 nm and 280 nm. Plasmid preparations with A260/A280 ratios between about 1.75 and about 2.00 are suitable for producing the Fc-fusion constructs.

The expression vector pTT5 allows for extrachromosomal replication of the cDNA driven by a cytomegalovirus (CMV) promoter. The plasmid vector pcDNA-pDEST40 is a Gateway-adapted vector which can utilize a CMV promoter for high-level expression. SuperGlo GFP variant (sgGFP) can be obtained from Q-Biogene (Carlsbad, Calif.). Preparing a pCEP5 vector can be accomplished by removing the CMV promoter and polyadenylation signal of pCEP4 by sequential digestion and self-ligation using SalI and XbaI enzymes resulting in plasmid pCEP4Δ. A GblII fragment from pAdC-MVS (Massie et al., J. Virol. 72:2289-2296 (1998)), encoding the CMV5-poly(A) expression cassette ligated in BglII-linearized pCEP4Δ, resulting in the pCEP5 vector.

Vectors for expressing Fc-fusion polypeptides can include those comprising vectors optimized for use in CHO-S or CHO-S-derived cells, such as pDEF38 (CHEF1) and similar vectors (Running Deer et al., Biotechnol. Prog. 20:880-889 (2004)). The CHEF vectors contain DNA elements that lead to high and sustained expression in CHO cells and derivatives thereof. They may include, but are not limited to, elements that prevent the transcriptional silencing of transgenes.

Fc-fusion molecule polynucleotide vectors may be joined to a selectable marker for propagation in a host. Generally, a selectable marker allows the selection of transformed cells based on their ability to thrive in the presence or absence of a chemical or other agent that inhibits an essential cell function. The selectable markers confer a phenotype on a cell expressing the marker, so that the cell can be identified under appropriate conditions. Suitable markers, therefore, include genes coding for proteins which confer drug resistance or sensitivity thereto, impart color to, or change the antigenic characteristics of those cells transfected with a molecule encoding the selectable marker, when the cells are grown in an appropriate selective medium.

Suitable selectable markers include dihydrofolate reductase or G418 for neomycin resistance in eukaryotic cell culture; and tetracycline, kanamycin, or ampicillin resistance genes for culturing in *E. coli* and other bacteria. Suitable selectable markers also include cytotoxic markers and drug resistance markers, whereby cells are selected by their ability to grow on media containing one or more of the cytotoxins or drugs; auxotrophic markers, by which cells are selected for their ability to grow on defined media with or without particular nutrients or supplements, such as thymidine and hypoxanthine; metabolic markers for which cells are selected, for example, for ability to grow on defined media containing a defined substance, for example, an appropriate sugar as the sole carbon source; and markers which confer the ability of cells to form colored colonies on chromogenic substrates or cause cells to fluoresce.

As mentioned above, vectors for the expression of Fc-fusion polypeptides can also be constructed in retroviral vectors. One such vector, the ROSA geo retroviral vector, which maps to mouse chromosome six, was constructed with the reporter gene in reverse orientation with respect to retroviral transcription, downstream of a splice acceptor sequence (U.S. Pat. No. 6,461,864; Zambrowicz et al., Proc. Natl. Acad. Sci. 94:3789-3794 (1997)). Infecting embryonic stem (ES) cells with ROSA geo retroviral vector resulted in the ROSA geo26 (ROSA26) mouse strain by random retroviral gene trapping in the ES cells.

A DNA insert comprising an Fc-fusion molecule can be operatively linked to an appropriate promoter, such as the phage lambda PL promoter; the *E. coli* lac, trp, phoA, and tac promoters; the SV40 early and late promoters; and promoters of retroviral LTRs. Suitable promoters also include the pCMV vector with an enhancer, pcDNA3.1; the pCMV vector with an enhancer and an intron, pCIneo; the pCMV vector with an enhancer, an intron, and a tripartite leader, pTT2, and CHEF1. Other suitable promoters will be known to the skilled artisan. The promoter sequences include the minimum number of bases or elements necessary to initiate transcription of a gene of interest at levels detectable above background. Within the promoter sequence may be a transcription initiation site, as well as protein binding domains (consensus sequences) responsible for the binding of RNA polymerase. Eukaryotic promoters of the invention will often, but not always, contain "TATA" boxes and "CAT" boxes.

The invention provides vectors for the in vivo expression of Fc-fusion polypeptides in animals, including humans, under the control of a promoter that functions in a tissue-specific manner. For example, promoters that drive the expression of CSF-1R fusion proteins of the invention may be liver-specific, as described in PCT/US06/00668.

A region of additional amino acids, particularly charged amino acids, may be added to the N-terminus of the polypeptide to improve stability and persistence in the host cell purification throughout and subsequent handling and storage. Also, amino acid moieties may be added to the polypeptide to facilitate purification. Such amino acids may or may not be removed prior to the final preparation of the polypeptide. The Fc-fusion proteins of the invention can be fused to marker sequences, such as a peptide, that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., Proc. Natl. Acad. Sci. 86:821-824 (1989), for instance, hexa-histidine provides for convenient purification of the fusion protein. Another peptide tag useful for purification, the hemagglutinin HA tag, corresponds to an epitope derived from the influenza hemagglutinin protein (Wilson et al., Cell 37:767-778 (1984)). Any of the above markers can be engineered using the polynucleotides or the polypeptides of the present invention.

The expression constructs of the invention will further contain sites for transcription initiation, termination, and, in the transcribed region, a ribosome binding site for translation. The coding portion of the transcripts expressed by the constructs can include a translation initiating codon at the beginning and a termination codon (UAA, UGA, or UAG) appropriately positioned at the end of the polypeptide to be translated.

Host Cell and Method of Expression

In yet another aspect, the present invention provides a cell line comprising the nucleic acid that encodes the fusion polypeptide. In some embodiments, the cell line transfected may be a prokaryotic cell line, a eukaryotic cell line, a yeast cell line, an insect cell line, an animal cell line, a mammalian cell line, a human cell line, etc. The proteins expressed in mammalian cells have been glycosylated properly. The mammalian cells are preferred to produce the fusion proteins in this disclosure. Examples of useful mammalian host cell lines are HEK293, CHO, sp2/0, NS0, COS, BHK, PerC6. Many other cells can also be used as the expression and production host, and hence, are encompassed by this disclosure.

For recombinant production of the fusion proteins, molecular cloning method is used based on the molecular cloning protocols, e.g., Sambrook & Russel, Molecular Cloning ($3^{rd}$ ed., CSHL Press, 2001). The DNA sequences coding the fusion protein can be acquired by ordinary techniques, e.g. by whole gene synthesizing or spliced from Flt1 and KDR DNA fragments. Many vectors can be used. The vector components generally include, but are not limited to, one or more of the following: a signal sequence for the secretion of expressed proteins, one or more marker genes including the selection marker gene for the stable cell line screening in eukaryote cells, an origin of replication, an enhancer element, a promoter, and a transcription termination sequence, and poly A, etc.

Transfection of animal cells typically involves opening transient pores or "holes" in the cell membrane, to allow the uptake of material. Genetic material (such as supercoiled plasmid DNA or siRNA constructs), or even proteins such as antibodies, may be transfected. There are various methods of introducing foreign DNA into a eukaryotic cell. Transfection can be carried out using calcium phosphate, by electroporation, or by mixing a cationic lipid with the material to produce liposomes, which fuse with the cell membrane and deposit their cargo inside. Many materials have been used as carriers for transfection, which can be divided into three kinds: (cationic) polymers, liposomes and nanoparticles.

The recombinant fusion polypeptide may be recovered from the cells by precipitation, ultracentrifugation, or chromatographic methods, including ion exchange chromatography, size exclusion chromatography, affinity chromatography, immunoaffinity chromatography, HPLC, etc. RP-HPLC may be used to further purify the recovered fusion protein. When the fusion protein is secreted, commercially available ultrafiltration membranes from Millipore, Amicon, Pellicon, etc. may be used to concentrate the supernatant.

In some embodiments, protein A affinity chromatography may be used to recover the recombinant fusion polypeptide. Protein A is a cell wall component produced by several strains of *Staphylococcus aureus* and can be made in a recombinant fashion. It consists of a single polypeptide chain weighing approximately 42,000 daltons and contains little or no carbohydrate. Protein A binds specifically to the Fc region of most immunoglobulin molecules, including IgG (Sjoquist et al., Eur. J. Biochem. 29:572-578 (1972); Hjelm et al., Eur. J. Biochem. 57:395-403 (1975)).

Protein G affinity chromatography may also be used to purify Fc-fusion polypeptides of the invention. Protein G is a bacterial cell wall protein produced by group G streptococci and can also be made in a recombinant fashion. Like Protein A, Protein G binds to most mammalian immunoglobulins, primarily through their Fc regions (Bjorck et al., J. Immunol. 133:969-974 (1984); Guss et al., EMBO J. 5:1567-1575 (1986); Åkerström et al., J. Biol. Chem. 261:10,240-10,247 (1986)). Affinity chromatography using chimeric Fc binding molecules may further be used to purify Fc-fusion polypeptides of the invention. For example, Protein A/G is a genetically engineered protein that combines the IgG binding profiles of both Protein A and Protein G. Protein A/G is a gene fusion product, which can be secreted from, inter alia, non-pathogenic *Bacillus*. Protein A/G typically weighs approximately 50,000 daltons and was designed to contain four Fc binding domains from Protein A and two from Protein G (Sikkema, Amer. Biotech. Lab. 7:42 (1989); Eliasson et al., J. Biol. Chem. 263:4323-4327 (1988)).

The role of the fusion proteins in this disclosure is to block the VEGF signal pathway, and these proteins can be used in the therapy for pathological angiogenesis or VEGF over expression diseases. These diseases include (but are not limited to) solid tumors, age-related macular degeneration (AMD), rheumatoid arthritis, diabetic retinopathy, etc. The fusion protein can be delivered into human body with purified proteins from fermentation, or by gene therapy method. Therefore, the application of the fusion proteins of this disclosure is not limited to the fusion protein forms, but also includes the encoding DNA sequence formats, and so on.

Pharmaceutical Composition

This disclosure also includes a pharmaceutical composition which contains the fusion proteins of this disclosure. The mixture comprises optional physiologically acceptable carriers, excipients or stabilizers. The mixture pharmaceutical preparation maybe in any form including preferred lyophilized formulation, the preferred is in the form of parenteral injections. The mixture pharmaceutical preparation can be prepared by conventional pharmaceutical pharmacy method. Therapeutic formulations of the fusion proteins are prepared for storage by mixing the fusion protein having the desired degree of purity with optional physiologically acceptable carriers, excipients or stabilizers, in the dosage forms needed.

Also provided in this disclosure is a method for blocking angiogenesis, treating a VEGF-related disease or inhibiting tumor growth, which method comprises administrating to a subject an effective amount of the pharmaceutical composition comprising the fusion protein. Any tumor which involves angiogenesis during its initiation or progression may be treated with the present invention.

A "therapeutically effective amount" is at least the minimum concentration required to effect a measurable improvement of a particular symptom, such as that associate with cancer. A therapeutically effective amount herein may vary according to factors such as the disease state, age, sex, and weight of the patient. A therapeutically effective amount is also one in which any toxic or detrimental effects of the pharmaceutical composition are outweighed by the therapeutically beneficial effects.

The composition may be administered using any formula suitable for mammals, such as capsules, pills, injections, emulsions, suppository, and the like. Injections are preferred. When used, a therapeutically effective amount of the composition is administered to a mammal (e.g., human). Such therapeutically effective amount is usually at least about 0.1 μg/kg body weight, and usually not more than about 50 mg/kg body weight, preferably about 1 μg-about 10 mg/kg body weight. Of course, path of administration and patient condition should also be considered in deciding dose of administration, which is within the knowledge of medical practitioners.

The present invention may be used alone or in combination with other therapeutics for the treatment of angiogenesis related diseases such as tumor. When administered, the composition may be used locally or through whole-body administration, depending on the type, location, and stage of the disease.

EXAMPLES

The following examples are offered to illustrate but not to limit the invention.

Example 1

Construction of Fusion Proteins and Expression Vectors

The amino acid sequences of candidate proteins were obtained from the GenBank for Flt1 (NP_002010.2) and KDR (NP_002244). These candidate protein domains were fused to the amino acid sequence of human IgG1 Fc (P01857, 104-330). Signal peptide comes from Flt1 (NP_002010:1-26). FIG. 2 exhibits the schematic structures of fusion proteins SR1-3.

Figure 3:
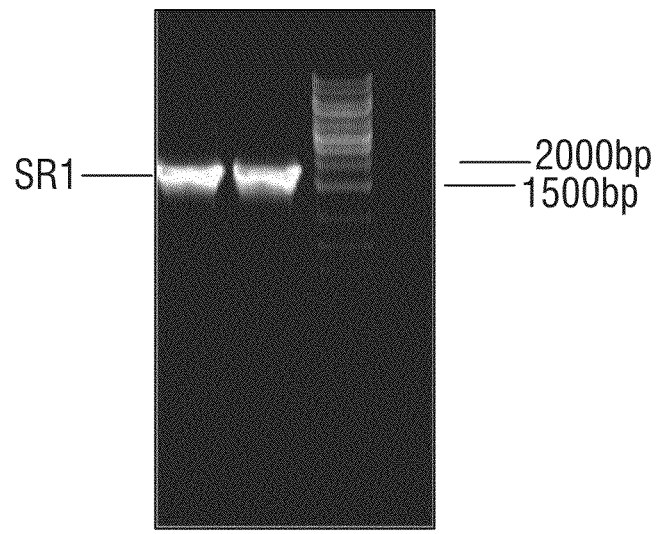
FIG. 3 shows the agarose gel electrophoresis results of the 1800 by SR1 target fragment constructed by PCR.

Recombinant DNA sequences were obtained by molecular cloning techniques, and inserted into the expression vector pcDNA3.1 after XbaI/HindIII restriction enzyme sites were added. The constructed recombinant DNA is run on an agarose gel and the result is shown in FIG. 3.

Example 2

Expression and Purification of Fusion Proteins

After transient transfection of the expression vector into a cell line, the fusion proteins were expressed and purified. Once the fusion protein proved effective in animal models, the suitable expression vector was transferred into a CHO cell line. Highly expressing clones were selected and expression and purification of the fusion proteins from stable CHO cells were performed. The stable cell line with a relative high titer was used for manufacturing.

Transient Cell Expression

Well-grown exponential stage Freestyle 293F cells were seeded at a density of $1 \times 10^6$/ml. The following day, Vector DNA was mixed with Freestyle MAX Reagent at 1:1.2 ratio and kept at room temperature for 10-15 minutes, then added to the media slowly. Cells were incubated at 37° C., 8% $CO_2$ concentration, and shaken at 135 rpm for three days. The culture medium was harvested and fusion protein purified with a Protein A affinity column.

Purified fusion proteins were run on denaturing and non-denaturing SDS PAGE gels which are shown in FIG. 4(A), (B).

Purified proteins were separated on non-denaturing SDS-PAGE electrophoresis, followed by Western blot analysis with goat anti human IgG Fc-HRP, diluted at 1:1000 for one hour at 37° C. After sufficient wash, the blot was visualized with DAB and photographed.

Results from the Western blot analysis is shown in FIG. 5.

Stable Cell Expression

Using a BioRad electroporator, 30 μg of vector DNA was mixed with $1 \times 10^7$ DG44 cells, incubated on ice to 10-15 minutes, and electroporated once at 300 V, 900 μF. Cells were inoculated at $5 \times 10^4$/ml in 96-well plates at 100 μl/well. MTX were added after three days. Medium was changed every 5 days. After 14 days, single clones were selected and expanded. Clone #5 has the highest expression level of about 100 mg/l.

Non-denaturing SDS-PAGE of 20 nl supernatant from culturing flask is shown in FIG. 6.

Example 3

In Vitro Binding Assay of Fusion Proteins

Binding Ability of Fusion Proteins with VEGF

Binding assay of fusion proteins with VEGF were performed by quantitative ELISA kit using VEGF-Trap as control. Fusion proteins were mixed in serial concentrations with 40 pM human $VEGF_{165}$, and incubated at 37° C. for 1 hour. After washing, goat anti human IgG Fc-HRP was added and TMB visualization was performed. The $EC_{50}$ for the fusion protein SR1 and VEGF-Trap was calculated.

Figure 7:
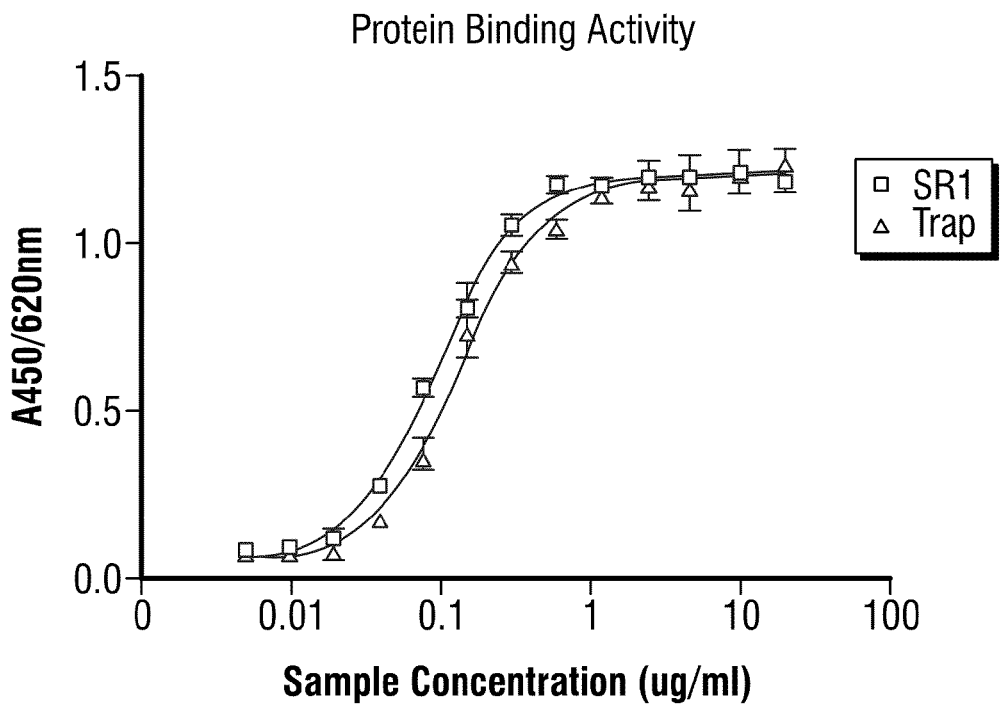
FIG. 7 shows results from the in vitro binding assay.

Results from the in vitro binding assay are shown in FIG. 7. From the initial results, the fusion protein SR1 has a higher binding affinity to VEGF with an $EC_{50}$ of 0.092 μg/ml, in comparison, VEGF-Trap has an $EC_{50}$ of 0.136 μg/ml.

Binding Stoichiometry of SR1 with VEGF Using BIACcore™

SR1 was captured with an anti-Fc specific antibody that is first immobilized on a BIACcore™ chip using amine-coupling chemistry. A blank antibody surface was used as a negative control. $VEGF_{165}$ was injected at a concentration of 1 nM, 10 nM, and 50 nM over the SR1 surfaces at 10 μl/min for one hour. A real-time binding signal was recorded and saturation binding was achieved at the end of each injection. Binding stoichiometry was calculated as a molar ratio of bound $VEGF_{165}$ to the immobilized SR1.

In solution, SR1 at a concentration of 1 nM was mixed with varied concentrations of $VEGF_{165}$. After one hour incubation, concentrations of the free SR1 in solution were measured as a binding signal to an amine-coupled $VEGF_{165}$ surface. A calibration curve was used to convert the SR1 BIACcore™ binding signal to its molar concentration. Binding stoichiometry was calculated as a molar ratio of bound $VEGF_{165}$ to the immobilized SR1.

Figure 8:
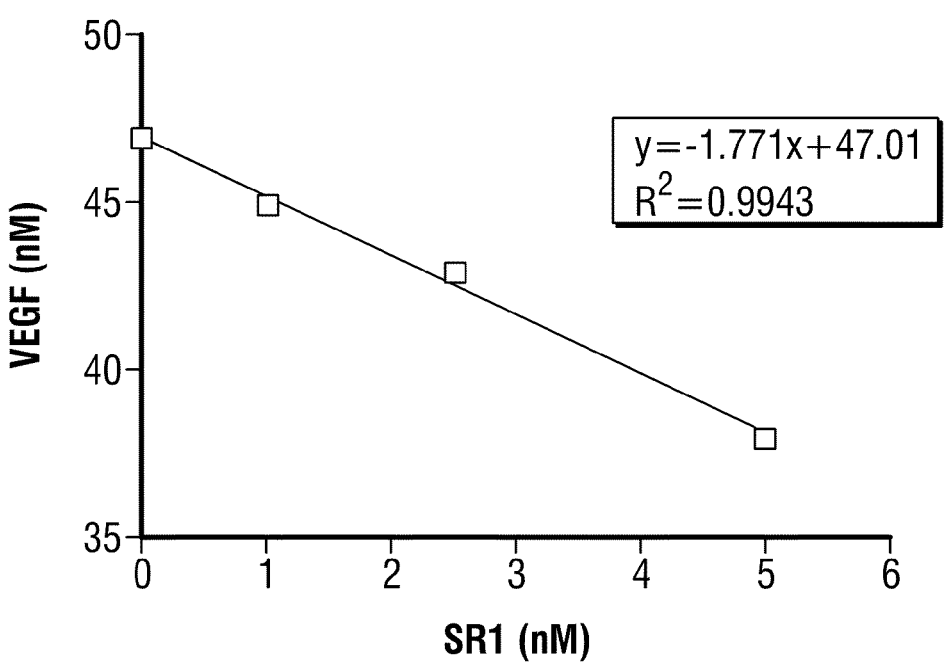
FIG. 8 shows the results from the binding stoichiometry assay of SR1 with VEGF using BIACore™.

Results from the BIACcore™ experiments are shown in FIG. 8.

Endothelial Cell Growth Assay

Well-grown human umbilical cord vein endothelial cells (HUVEC, Cambrex Bio Science Walkersville, Inc.) was harvested, and seeded in 96 well plates at $4-8 \times 10^4$ cells/ml, 100 μl/well, in EGM basal medium (Cambrex), then grown for 24 hours in humidified incubator (37±1° C., 50% humidity). Fusion proteins and positive control VEGF-Trap were diluted with 2% FBS to concentrations about 140 μg/ml, $VEGF_{165}$ was diluted to a concentration at about 400 ng/ml with 2% FBS, and were diluted by half eight times. Media were removed from the 96 well plates and samples were added at 100 μl/well. After another 72 hours of incubation, 10 μl CCK-8 was added to each well, followed by incubation for 2.5 hours. Absorptions at wavelength 450 nm and referenced at 650 nm were detected, using no cell negative control well as blank.

PIGFII (construct cDNA according to the sequence information from GenBank Accession number AAD30179, add 6×His encoding sequence to 3' end, insert into pcDNA4 vector (Invitrogen), express in 293F cell line, recover with Ni-Sepharose) was diluted with base media with 2% FBS to 4000 ng/ml. Fusion proteins and positive control VEGF-Trap were diluted with 2% FBS to concentrations about 300 μg/ml, and were diluted by half eight times. Media were removed from the 96 well plates and samples were added at 100 μl/well. After another 72 hours of incubation, 10 μl CCK-8 was added to each well, followed by incubation for 2.5 hours. Absorptions at wavelength 450 nm and referenced at 650 nm were detected, using no cell negative control well as blank.

Figure 9A:
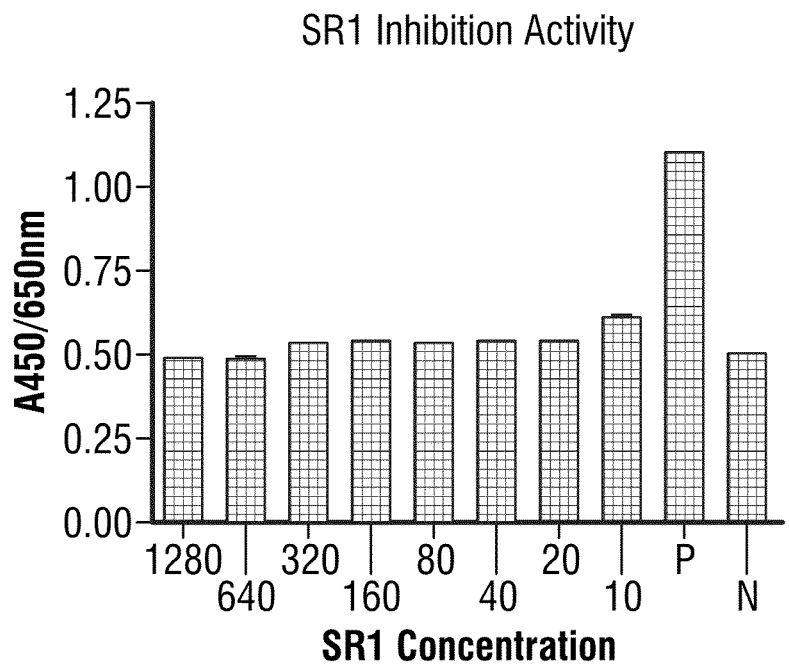
FIGS. 9A-B show results from the endothelial cell growth assay for the inhibitory effects of SR1 and VEGF-Trap on VEGF. Positive control contains VEGF but no SR1 or VEGF-Trap. Negative control is sample solution only.
Figure 9B:
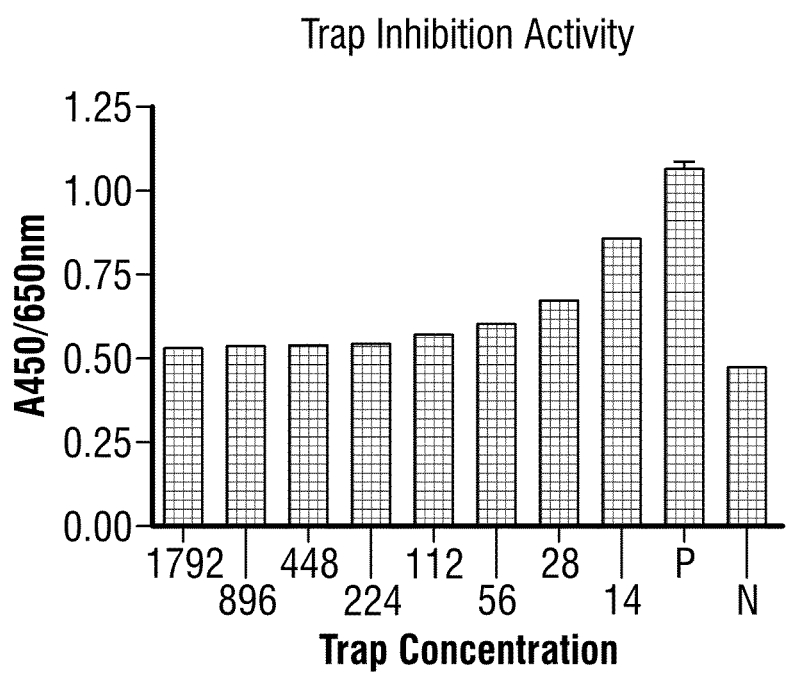
Figure 10A:
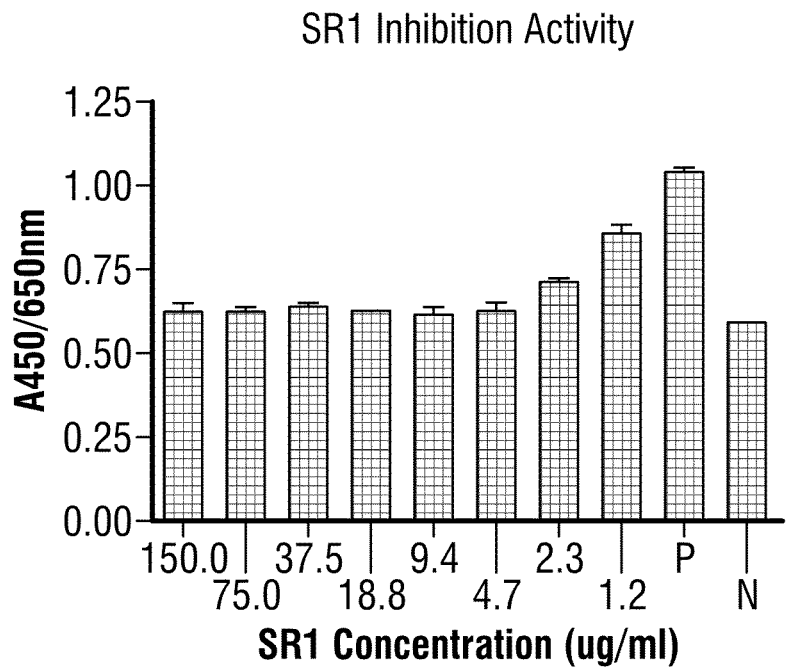
FIGS. 10A-B show results from the endothelial cell growth assay for the inhibitory effects of SR1 and VEGF-Trap on PlGF. Positive control contains PlGF but no SR1 or VEGF-Trap. Negative control is sample solution only.
Figure 10B:
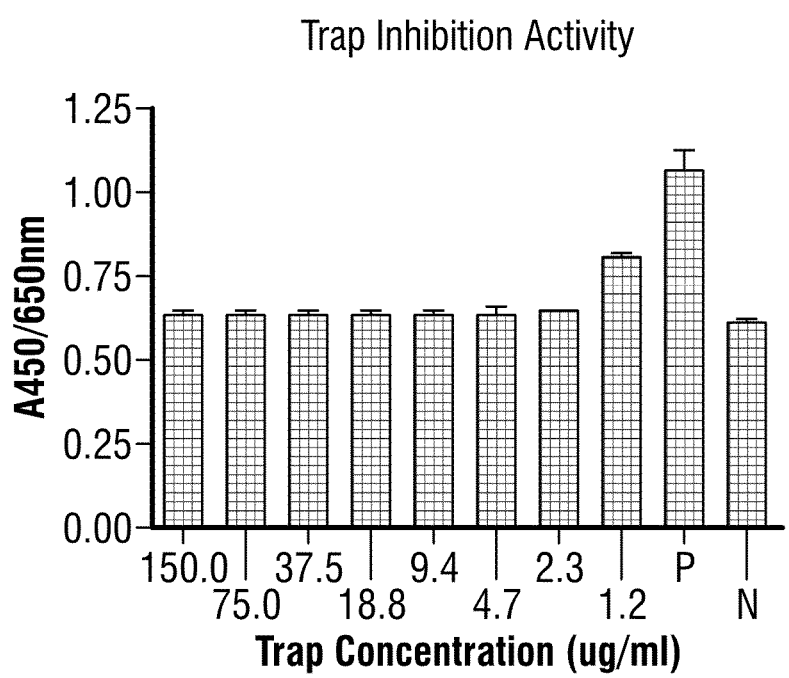
Figure 11A:
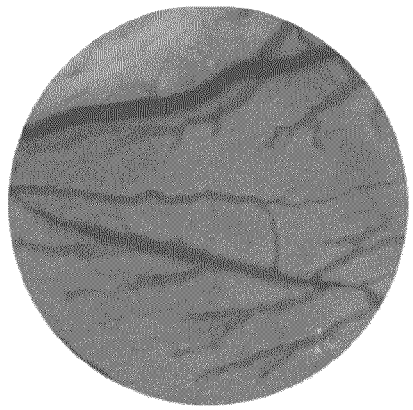
FIGS. 11A-D show results from in vivo anti-angiogenesis activity assays using chorioallantoic membrane (CAM).
Figure 11B:
Figure 11C:
Figure 11D:
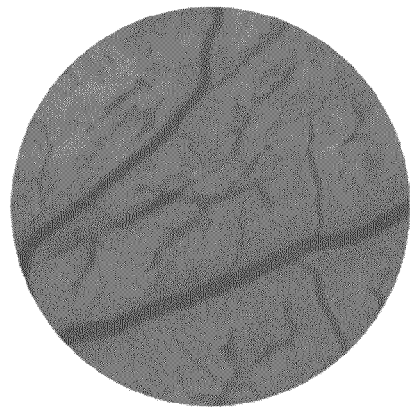

Results from the endothelial cell growth assay are shown in FIGS. 9 and 10. From the results, the fusion proteins SR1 and VEGF-Trap completely inhibited the growth activity of VEGF on HUVEC at a concentration of 20 pM and 28 pM, respectively. The fusion protein SR1 retained most of the inhibitory activity against VEGF at 10 pM. In contrast, VEGF-Trap retained about half of its inhibitory activity against VEGF at 14 pM. Therefore, SR1 is more effective than VEGF-Trap for inhibiting the angiogenic activity of VEGF.

Example 4

In Vivo Anti-Angiogenesis Activity Assay of Fusion Proteins

Equipments and filter paper used for surgery were sterilized. Fertilized chick eggs were placed in humidified atmosphere (37±1° C., 50% humidity) for 6 days. On the sixth day, egg viability was checked and viable eggs were cut open. The location of chorioallantoic membrane (CAM) was identified under light and labeled. A hole was cut at the end of the egg that the CAM was located, with the CAM side up. The CAM was separated from the egg shell, and then was cut to form a window of 1 cm$^2$. The filter paper was added with 10 μl of sample, dried, and placed lightly on the CAM without touching a major blood vessel. The window was closed with tape and the egg was incubated for 48 hours. Later, the window was enlarged and photographed under a microscope. Angiogenesis was scored according to new banches of the blood vessels. The fusion protein SR1 was dosed at 0.4 μg, 2 μg, and 10 μg, while VEGF-Trap control was dosed at 10 μg.

Results from the CAM experiments are shown in Table 1 and FIG. 11. According to the experimental results summarized in Table 1 and shown in FIG. 11, under the same concentration of 10 μg/ml, SR1 has similar anti-angiogenesis activity against CAM.

TABLE 1

Inhibition of angiogenesis in chicken embryo chorioallantoic membrane by fusion proteins

| Group | Dose | Sample | Number of new blood vessels | Inhibition (%) |
| --- | --- | --- | --- | --- |
| SR1 High-dose | 10 μg | 7 | 13.00 ± 1.41** | 40.33 |
| SR1 middle-dose | 2 μg | 9 | 15.89 ± 3.55$^\Delta$ | 30.49 |
| SR1 low-dose | 0.4 μg | 7 | 17.00 ± 5.54**$^\Delta$ | 22.44 |
| Trap control | 10 μg | 7 | 12.43 + 2.57** | 44.67 |
| PBS control | 10 μl | 8 | 22.50 ± 3.24 | |

Inhibition (%) = (1 − new blood vessels in sample group/blood vessels in control group) × 100%.
**$p < 0.05$ vs. PBS negative control.
$^\Delta p < 0.05$ vs. positive control.

Example 5

In Vivo Tumor Inhibition Assay

Well cultivated human A673 rhabdomyosarcoma cells (ATCC; CRL 1598) were suspended in normal saline. Female BALB/c nude mice, 6-10 weeks old, were injected subcutaneously with 1×10$^6$ tumor cells in the dorsal area in a volume of 100 μl. Twenty-four hours after tumor cell inoculation, animals were then treated with fusion protein SR1, or Avastin® (Roche, 3615286 HK 0508.1070). Both fusion protein and control were administered at the doses of 400 μg, twice weekly. Each group consisted of 4 mice. Tumor size was determined at weekly intervals. Four weeks after tumor cell inoculation, animals were euthanized and the tumors were removed and weighed.

Results from the tumor inhibition experiments are shown in Table 2.

TABLE 2

Inhibitory effects by SR1 on tumor size from transplanted LS174T human colon cancer cells in nude mice

| Group | Average Tumor Weight after 28 Days (mg) |
| --- | --- |
| Avastin | 1173.93 ± 944.34 (n = 4) |
| SR1 | 481.34 ± 272.82 (n = 4) |
| Model Control | 2138.25 ± 1030.21 (n = 4) |

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Citation of the above publications or documents is not intended as an admission that any of the foregoing is pertinent prior art, nor does it constitute any admission as to the contents or date of these publications or documents.

What is claimed is:

1. A fusion protein comprising a chimeric VEGF receptor or a fragment thereof and a multimerizing component, wherein the chimeric VEGF receptor or the fragment thereof comprises at least two immunoglobulin-like domains from different VEGF receptors, one being the immunoglobulin-like domain 2 of the extracellular domain of KDR (KDRD2) as set forth in amino acids 12-95 of SEQ ID NO:2, another being the immunoglobulin-like domain 2 of the extracellular domain of Flt1 (Flt1D2) as set forth in amino acids 21-96 of SEQ ID NO:1, and the fusion protein binds with high affinity to VEGF.

2. The fusion protein of claim 1, wherein the chimeric VEGF receptor or fragment thereof further comprises the immunoglobulin-like domain 3 of the extracellular domain of KDR (KDRD3) as set forth in amino acids 114-202 of SEQ ID NO:2.

3. The fusion protein of claim 2, wherein the fusion protein is a recombinant fusion protein.

4. The recombinant fusion protein of claim 3, wherein the VEGF receptor immunoglobulin-like domains are from multiple species.

5. The recombinant fusion protein of claim 3, wherein the VEGF receptor immunoglobulin-like domains are from the same species.

6. The recombinant fusion protein of claim 5, wherein the VEGF receptor immunoglobulin-like domains are from human.

7. The recombinant fusion protein of claim 3, wherein the fusion protein binds with high affinity to placental growth factor (PIGF).

8. The recombinant fusion proteins of claim 3, wherein the multimerizing component comprises an Fc fragment of a human immunoglobulin.

9. The recombinant fusion protein of claim 8, wherein the human immunoglobulin is selected from the group consisting of IgG, IgM and IgA.

10. The recombinant fusion protein of claim 9, wherein the IgG is selected from the group consisting of IgG1, IgG2, IgG3 and IgG4.

11. The recombinant fusion protein of claim 10, wherein the fusion protein comprises the amino acid sequence set forth in SEQ ID NO:6.

12. The recombinant fusion protein of claim 3, wherein the Flt1D2 is not directly linked to the KDRD3 in the chimeric VEGF receptor or fragment thereof.

13. A composition, which composition comprises:
 a) a fusion protein of claim 1; and
 b) a PIGF molecule,
 wherein the fusion protein binds with high affinity to the PIGF molecule through the chimeric VEGF receptor or fragment thereof.

14. The composition of claim 13, wherein the chimeric VEGF receptor or fragment thereof binds to the PIGF molecule bivalently.

15. A method of making a pharmaceutical composition, which method comprises combining the fusion protein of claim 1 with a pharmaceutically acceptable carrier, adjuvant or diluent.

16. A pharmaceutical composition comprising a fusion protein comprising a chimeric VEGF receptor or a fragment thereof and a multimerizing component, wherein the chimeric VEGF receptor or the fragment thereof comprises at least two immunoglobulin-like domains from different VEGF receptors, one being the immunoglobulin-like domain 2 of the extracellular domain of KDRD2 as set forth in amino acids 12-95 of SEQ ID NO:2, another being the immunoglobulin-like domain 2 of the extracellular domain of Flt1 (Flt1D2) as set forth in amino acids 21-96 of SEQ ID NO:1, and the fusion protein binds with high affinity to VEGF, and a pharmaceutically acceptable carrier, adjuvant or diluent.

17. A kit comprising, in one or more containers, the fusion protein of claim 1 or the pharmaceutical composition of claim 16.

18. A method for inhibiting angiogenesis in a subject in need thereof, comprising administering to the subject an effective amount of the pharmaceutical composition of claim 16.

* * * * *